United States Patent
Wagner et al.

(10) Patent No.: US 7,261,562 B2
(45) Date of Patent: Aug. 28, 2007

(54) WATER-INDICATING ENDODONTIC MONITORING DEVICES

(75) Inventors: Jeff Wagner, Salt Lake City, UT (US); Erich Haschke, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 10/718,755

(22) Filed: Nov. 21, 2003

(65) Prior Publication Data

US 2005/0112528 A1    May 26, 2005

(51) Int. Cl.
*A61C 5/02* (2006.01)

(52) U.S. Cl. .......................................... 433/224; 433/81

(58) Field of Classification Search ................ 433/224, 433/81

See application file for complete search history.

(56) References Cited

U.S. PATENT DOCUMENTS

| | | | |
|---|---|---|---|
| 4,359,455 A * | 11/1982 | Nakamura et al. ............ 435/34 |
| 5,290,172 A | 3/1994 | Sakuma et al. ............. 433/215 |
| 5,725,373 A | 3/1998 | Yeh .............................. 433/72 |
| 6,482,009 B1 * | 11/2002 | Rubin .......................... 433/224 |
| 6,559,351 B1 * | 5/2003 | Eakin .......................... 602/56 |
| 6,576,473 B1 | 6/2003 | Scaringe et al. |
| 2002/0081550 A1 | 6/2002 | Karazivan ..................... 433/80 |
| 2003/0008264 A1 | 1/2003 | Rubin ......................... 433/224 |

OTHER PUBLICATIONS

Dtsch Zahnarzt Z., 45(4): 222-6 1991 "Drying of Root Canals" Database: PubMed, Accesseion No.: 91078238.

* cited by examiner

*Primary Examiner*—Cris Rodriguez
*Assistant Examiner*—Candice C Stokes
(74) *Attorney, Agent, or Firm*—Workman Nydegger

(57) ABSTRACT

Water-indicating endodontic monitoring devices include an endodontic cone formed of a water absorptive material, and a chemical indicator comprising at least one cobalt salt applied to the water absorptive material. Alternatively, the water-indicating endodontic points may include a pH-changing material and a pH-sensitive indicator. The devices are manufactured by applying an aqueous solution that includes a moisture sensitive color-changing chemical indicator to the endodontic cone. The solution may be applied by spraying, dipping, or otherwise coating or impregnating the material. Once applied, the endodontic cones are dried so as to be substantially free of moisture. In use, the endodontic cone may be inserted into the root canal of a patient, and when withdrawn, a change in the color of the chemical indicator indicates the presence of moisture within the root canal. The endodontic cone may optionally change to a different color in order to indicate the presence of aqueous sodium hypochlorite within the root canal.

17 Claims, 2 Drawing Sheets

Dark Blue

Bright Pink

WATER-INDICATING ENDODONTIC MONITORING DEVICES

BACKGROUND OF THE INVENTION

1. The Field of the Invention

The present invention relates to endodontics, more particularly to a device and method for easily determining whether moisture is present within the root canal of a tooth prior to sealing the root canal.

2. The Relevant Technology

When a dental practitioner performs a root canal, pulp and other material in the root canal chamber is removed. Once a dentist has removed diseased and soft tissue from a tooth's root canal, the chamber must be filled. Before the canal can be filled with gutta percha or another suitable material, any moisture present within the canal must be removed. It is important to remove the moisture, which could otherwise result in bacterial infection of the chamber. Moisture can also inhibit bonding between the root canal walls and a sealant, if used.

In some instances, pressurized air has been used to dry the canal, but because the source of pressurized air often contains even a small amount of moisture that can condense in the canal, use of this method is discouraged.

Dental practitioners have attempted to dry the canal by using cotton swabs or paper points which can be inserted down into the canal. Because of the large size of cotton swabs and the narrow cross sections of the canals, especially in the apical region, completely removing all of the moisture may prove difficult. Paper points are more easily inserted into the canal, and are especially useful as they are able to extend through curved and narrow portions of the canal, but it can still be difficult to determine whether all the moisture has been removed from the canal.

It would be an improvement in the art to provide a device and method which may be used to easily and accurately determine whether moisture is present within a root canal.

BRIEF SUMMARY OF THE INVENTION

The present invention relates to an endodontic device that can be used for detecting the presence of moisture within a root canal. According to one embodiment, the device comprises an endodontic cone formed of a water absorptive material and a chemical indicator comprising at least one cobalt salt applied to the water absorptive material. The chemical indicator changes color when moistened with water.

The endodontic cone may be formed of paper or other material that is water absorptive. The endodontic cone may be sprayed, dipped, or otherwise coated or impregnated with a moisture sensitive chemical indicator comprising at least one cobalt salt.

The chemical indicator may be applied as an aqueous solution. The solution may also include a wetting agent, such as ethanol, and/or a surfactant, such as Silwet. Once applied, the solution is allowed to dry so as to be substantially free of moisture. Once dried, the endodontic device is ready for use.

In use, the device may be inserted into the root canal of a patient's tooth. Because the device includes a color-changing chemical indicator, if moisture is present within the root canal, the chemical indicator will change color, indicating the presence of moisture. In this way, the practitioner is alerted to the presence of moisture within the root canal. If moisture is detected, the practitioner may insert additional devices into the root canal until the root canal is dry. The practitioner will be alerted that the canal is dry when the inserted device does not change color.

In addition to detecting the presence of moisture, it may sometimes be desirable to detect the presence of sodium hypochlorite. Once the practitioner abrades and cleans the pulp tissue out of the root canal, sodium hypochlorite may be introduced in order to disinfect the canal prior to drying and eventually sealing the canal. Once used to disinfect the canal, the sodium hypochlorite may then be rinsed out with water. Because of this, it may be desirable to use a device that includes a cobalt salt that also changes to a different color to indicate the presence of sodium hypochlorite. This allows the practitioner to be certain that all the sodium hypochlorite has been removed from the root canal chamber.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

The present invention relates to a device for detecting moisture within a root canal chamber. The device comprises an endodontic cone formed of a water absorptive material (e.g. paper) that includes a moisture sensitive chemical indicator applied to the water absorptive material. The chemical indicator comprises at least one cobalt salt that changes color when moistened with water.

II. Exemplary Device and Method of Manufacture

Figure 1A:
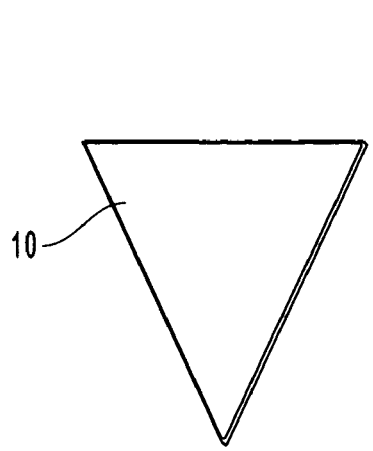
FIG. 1A is a perspective view of a piece of water absorptive material having a triangular shape.
Figure 1B:
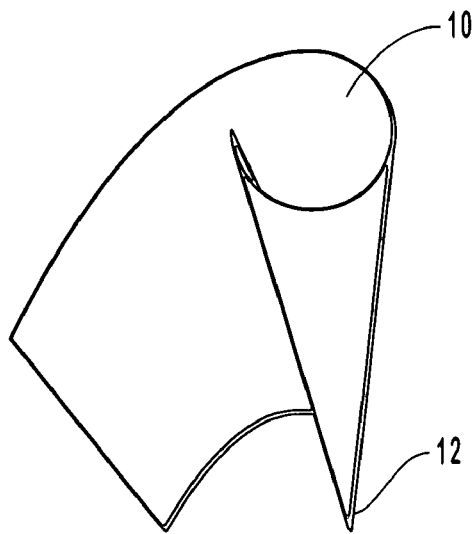
FIG. 1B is a perspective view of the water absorptive material of FIG. 1A, the material being partially rolled so as to form an endodontic cone.
Figure 2:
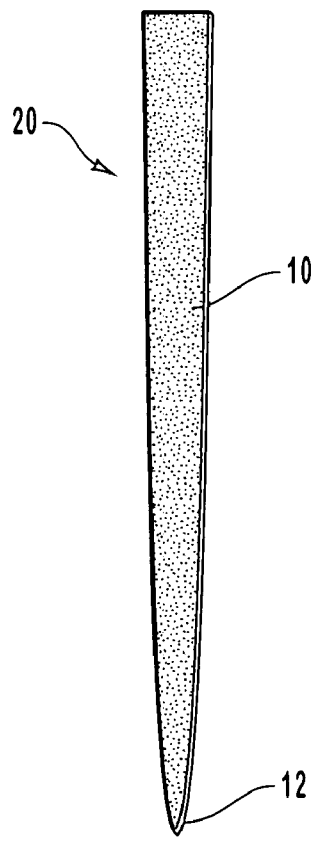
FIG. 2 is a perspective view of an exemplary device according to the present invention.

FIG. 1A is a perspective view of a piece of water absorptive material 10, such as paper. The material 10 is illustrated as having a generally triangular shape. FIG. 1B illustrates the water absorptive material 10 being rolled into a cone shape, having a tip 12 at one end, while FIG. 2 illustrates the water absorptive material 10 having been tightly rolled into an endodontic cone. The device 20, as illustrated in FIG. 2 comprises a water absorptive material 10 and a chemical indicator comprising at least one cobalt salt that is applied to the water absorptive material.

The chemical indicator comprises at least one cobalt salt. Suitable cobalt salts include various cobalt halides, such as cobalt fluoride, cobalt chloride, and cobalt iodide. Another suitable cobalt salt includes cobalt sulfate. Cobalt chloride is one particularly preferred cobalt salt. When dry, cobalt chloride is dark blue, and when exposed to moisture it turns a bright pink. If exposed to sodium hypochlorite, it turns black. The nature of the color changes, especially from dark blue to bright pink, are very pronounced, making it easy for the dental practitioner to recognize.

The chemical indicator may be applied as an aqueous solution that includes the color changing chemical indicator. The aqueous solution may include a wetting agent and/or a surfactant in addition to water and the chemical indicator comprising a cobalt salt. The cobalt salt may be included in an amount ranging from about 0.5% to about 50% by weight, preferably about 5% to about 40% by weight, and more preferably about 10% to about 30% by weight.

Ethyl alcohol may be included as a wetting agent, in an amount up to about 10%, preferably about 5%. Silwet may be included as a surfactant in an amount up to about 1%, preferably about 0.5%. The remainder of the aqueous solution comprises water (ranging from about 10% to about 99.5% by weight).

The aqueous solution may be applied by spraying, dipping, or otherwise coating or impregnating the water absorptive material 10 so that the chemical indicator is applied to the water absorptive material 10.

Once the aqueous solution has been applied, the material 10 with the applied aqueous solution are dried so as to be substantially free of moisture. It may be oven dried or allowed to air dry. The finished endodontic device 20 is illustrated in FIG. 2.

According to an alternative process for manufacturing a water indicating endodontic device, an aqueous pH changing solution is applied to the endodontic cone by spraying or dipping. The pH changing solution comprises a pH changing material (e.g. CaO, KOH, or $K_2CO_3$) in aqueous solution. In one embodiment, the pH changing material is present in an amount of about 0.01% to about 0.5% by weight. The treated endodontic cone is oven dried to produce a dry, treated endodontic cone. An anhydrous pH sensitive indicator solution comprising a pH sensitive color changing indicator (e.g. phenolphthalein) and an anhydrous volatile solvent (e.g. isopropanol or ethanol) is then applied to the endodontic cone by spraying or dipping. In one embodiment, the anhydrous pH sensitive indicator solution may comprise from about 0.01% to about 0.5% phenolphthalein. The endodontic cone is then allowed to dry.

In use, when water contacts the endodontic device for detecting moisture, the dried pH changing material (e.g. CaO) will cause the pH of the water to rise and react with the pH sensitive color-changing indicator (e.g. phenolphthalein) to change the color of the device, indicating moisture in the root canal chamber. In another embodiment, an acidic pH changing material, (e.g. citric acid) may be used with a pH sensitive color changing indicator that changes color at lower pH.

III. Exemplary Method of Use

Figure 3:
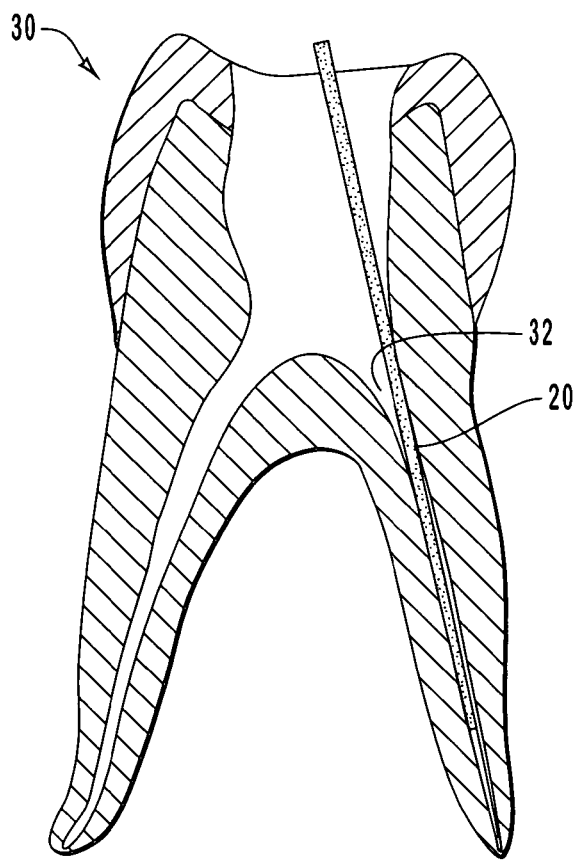
FIG. 3 is a cross sectional view of a patient's tooth with the device of FIG. 2 inserted into the root canal of the tooth.

FIG. 3 illustrates an exemplary tooth 30 where the root canal 32 has been treated using endodontic treatment devices and techniques known in the art. In one embodiment, the root canal 32 is further cleaned and disinfected using an antimicrobial rinse (e.g. a solution including sodium hypochlorite). Once the root canal 32 has been properly cleaned, the water-indicating device 20 is inserted into the root canal 32 in order to remove any residual moisture. Before inserting the device 20, the device 20 has a first color. For example, if the cobalt salt used is cobalt chloride, the device 20 has a dark blue color when dry and before insertion into the root canal 32.

The water absorbing material 10 of the device 20 may be paper, which is sufficiently flexible to allow the device 20 to be inserted through curved areas of the root canal chamber 32. If moisture is present within the root canal chamber, it will be absorbed by water-absorbing material 10, causing the chemical indicator that is on or impregnated into the material 10 to change color. In this manner, the device 20 serves both the purpose of removing residual water (and other residual materials such as sodium hypochlorite) from the canal, while also indicating to the dental practitioner whether or not moisture is present in the root canal 32.

Figure 4:
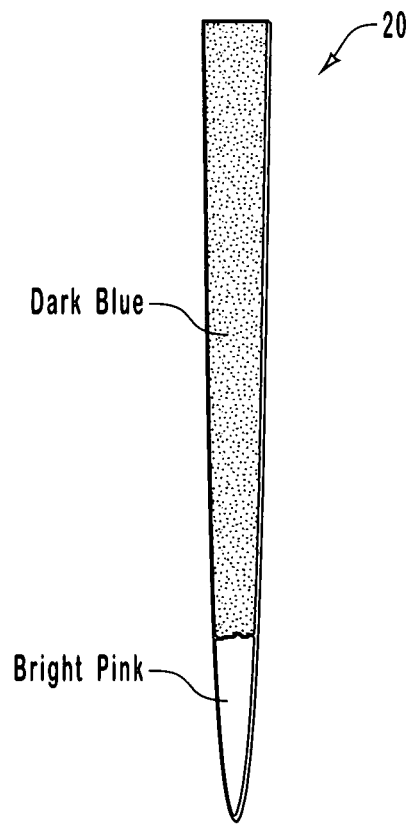
FIG. 4 is a perspective view of the device of FIG. 3 after withdrawing the device from the root canal.

The device 20 is then withdrawn from the root canal 32. A quick visual inspection by the dental practitioner will reveal whether the chemical indicator has changed color. FIG. 4 illustrates the device 20 after having been withdrawn from root canal 32. A portion of the device adjacent to the tip 12 has changed color, indicating the presence of moisture within the root canal chamber 32. For example, if the chemical indicator is cobalt chloride, it will change from a dark blue (dry condition) to a bright pink (wet condition) if moisture was present in the root canal chamber 32. If sodium hypochlorite was also present in the root canal chamber 32, the chemical indicator will instead change to black. If sodium hypochlorite is present in the root canal 32, it may be desirable to further rinse the root canal 32 with water until no more sodium hypochlorite is detected.

The dental practitioner may continue to insert and withdraw additional devices 20 from the root canal chamber 32 so as to remove any moisture remaining in the canal 32. When the withdrawn device has the same dark blue color as when inserted, the dental practitioner knows that the root canal 32 is dry, and may then proceed to seal the canal as known in the art.

IV. Examples of the Preferred Embodiments

The following are several examples of aqueous compositions according to the invention that can be used to manufacture water-indicating points. The exemplary formulations and manufacturing conditions are given by way of example, and not by limitation, in order to illustrate compositions that have been found to be useful for indicating the presence of water in a root canal. Unless otherwise indicated, all percentages are by weight.

EXAMPLE 1

An aqueous composition used to manufacture water-indicating points according to the invention was made by mixing together the following components:

| | |
|---|---|
| Cobalt Chloride | 20% |
| Ethyl Alcohol | 5% |
| Silwet | 0.5% |
| Water | 74.5% |

The aqueous composition was sprayed onto a plurality of paper points. The wetted points were then placed into an oven to dry. The dried water-indicating points were blue. When wetted with water they turned pink. When wetted with aqueous sodium hypochlorite, they turned black.

EXAMPLE 2

An aqueous composition used to manufacture water-indicating points according to the invention is made by mixing together the following components:

| | |
|---|---|
| Cobalt Chloride | 10% |
| Ethyl Alcohol | 10% |
| Silwet | 0.5% |
| Water | 79.5% |

The aqueous composition is used to manufacture a water-indicating point using the process of Example 1.

EXAMPLE 3

An aqueous composition used to manufacture water-indicating points according to the invention is made by mixing together the following components:

| | |
|---|---|
| Cobalt Chloride | 5% |
| Ethyl Alcohol | 15% |
| Silwet | 0.5% |
| Water | 79.5% |

The aqueous composition is used to manufacture a water-indicating point using the process of Example 1.

EXAMPLE 4

An aqueous composition used to manufacture water-indicating points according to the invention is made by mixing together the following components:

| | |
|---|---|
| Cobalt Chloride | 2% |
| Ethyl Alcohol | 15% |
| Silwet | 0.5% |
| Water | 82.5% |

The aqueous composition is used to manufacture a water-indicating point using the process of Example 1.

EXAMPLE 5

An aqueous composition used to manufacture water-indicating points according to the invention is made by mixing together the following components:

| | |
|---|---|
| Cobalt Chloride | 30% |
| Ethyl Alcohol | 5% |
| Silwet | 1% |
| Water | 64% |

The aqueous composition is used to manufacture a water-indicating point using the process of Example 1.

EXAMPLE 6

An aqueous composition used to manufacture water-indicating points according to the invention is made by mixing together the following components:

| | |
|---|---|
| Cobalt Chloride | 40% |
| Ethyl Alcohol | 4% |
| Silwet | 2% |
| Water | 54% |

The aqueous composition is used to manufacture a water-indicating point using the process of Example 1.

EXAMPLE 7

An aqueous composition used to manufacture water-indicating points according to the invention is made by mixing together the following components:

| | |
|---|---|
| Cobalt Chloride | 50% |
| Ethyl Alcohol | 2% |
| Silwet | 2% |
| Water | 46% |

The aqueous composition is used to manufacture a water-indicating point using the process of Example 1.

EXAMPLE 8

Any of the foregoing aqueous compositions is modified by replacing the cobalt chloride with one or more of cobalt fluoride, cobalt iodide or cobalt sulfate and then used to manufacture a water-indicating point.

EXAMPLE 9

A pH changing solution used to manufacture water-indicating points according to the invention was made by mixing together the following components:

| | |
|---|---|
| CaO | 0.1% |
| Water | 99.9% |

The pH changing solution was sprayed onto a plurality of paper points. The wetted points were then placed into an oven at about 105° C. to dry. The dried, treated paper points were then sprayed with an anhydrous pH sensitive indicator solution made by mixing together the following components:

| | |
|---|---|
| Phenolphthalein | 0.1% |
| Isopropanol | 99.9% |

The wet paper points were again allowed to dry. When wetted with water they turned from white to pink.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An endodontic device for detecting moisture within a root canal, comprising:
   an endodontic cone formed of a water absorptive material;
   a pH changing material applied to the water absorptive material; and
   a pH sensitive color changing indicator applied to the water absorptive material so as to not initially react with the pH changing material;
   wherein the endodontic device changes color when moistened with water and wherein the pH changing material causes water contacting the endodontic cone to either become substantially more basic than neutral or substantially more acidic than neutral so as to enhance a change in color of the endodontic device when the endodontic cone is moistened with water compared to a change in color of an endodontic device without the pH changing material.

2. An endodontic device as recited in claim 1, wherein the pH changing material is at least one base selected from the group consisting of an alkali metal oxide, alkali metal hydroxide, alkali metal carbonate, alkaline earth metal oxide, or alkaline earth metal hydroxide.

3. An endodontic device as recited in claim 2, wherein the pH changing material comprises at least one of CaG, KOH, and $K_2CO_3$.

4. An endodontic device as recited in claim 2, wherein the pH sensitive color changing indicator comprises phenolphthalein.

5. An endodontic device as recited in claim 1, wherein the pH changing material is at least one acid.

6. An endodontic device as recited in claim 5, wherein the at least one acid comprises citric acid.

7. An endodontic device as recited in claim 1, wherein the pH changing material is either strongly basic or strongly acidic when moistened with water.

8. A method of manufacturing an endodontic device for detecting moisture within a root canal, comprising the steps of:
   providing an endodontic cone comprising a water absorptive material;
   applying a pH changing solution that includes a pH changing material to the endodontic cone;
   drying the endodontic cone so as to be substantially free of moisture;
   applying an anhydrous pH sensitive indicator solution that includes a pH sensitive color changing indicator and an anhydrous volatile solvent to the endodontic cone;
   drying the endodontic cone so as to be substantially dry.

9. A method of manufacturing a device as recited in claim 8, wherein the endodontic cone is dried using an oven.

10. A method of manufacturing a device as recited in claim 8, wherein the pH changing material is present in the pH changing solution in an amount between about 0.01% and about 0.51% by weight.

11. A method of manufacturing a device as recited in claim 8, wherein the pH sensitive color changing indicator is present in the anhydrous pH sensitive indicator solution in an amount between about 0.01% and about 0.51%.

12. A method of manufacturing a device as recited in claim 8, wherein the anhydrous volatile solvent comprises one of isopropanol and ethanol.

13. A method of using a device for detecting moisture within a root canal, comprising the steps of:
   inserting an endodontic device within a root canal of a patient's tooth, the endodontic device comprising:
      an endodontic cone formed of a water absorptive material;
      a pH changing material applied to the water absorptive material; and
      a pH sensitive color changing indicator applied to the water absorptive material;
      wherein the endodontic device changes color when moistened with water,
      wherein the pH changing material enhances a change in color of the endodontic device when the endodontic cone is moistened with water compared to a change in color of an endodontic device without the pH changing material; and
   withdrawing the device and observing whether the chemical indicator has changed color, indicating the presence of moisture within the root canal.

14. An endodontic device for detecting moisture within a root canal, comprising:
   an endodontic cone formed of a water absorptive material;
   a pH changing material consisting of at least one base applied to the water absorptive material; and
   a pH sensitive color changing indicator applied to the water absorptive material;
   wherein the endodontic device changes color when moistened with water,
   wherein the base causes moisture contacting the endodontic cone to become significantly more basic than neutral in order to enhance a change in color of the endodontic device when the endodontic cone is moistened with water compared to a change in color of an endodontic device without the base.

15. An endodontic device as recited in claim 14, wherein the base causes moisture contacting the endodontic cone to become strongly basic.

16. An endodontic device for detecting moisture within a root canal, comprising:
   an endodontic cone formed of a water absorptive material;
   a pH changing material consisting of at least one acid applied to the water absorptive material; and
   a pH sensitive color changing indicator applied to the water absorptive material;
   wherein the endodontic device changes color when moistened with water,
   wherein the acid causes moisture contacting the endodontic cone to become substantially more acidic than neutral in order to enhance a change in color of the endodontic device when the endodontic cone is moistened with water compared to a change in color of an endodontic device without the acid.

17. An endodontic device as recited in claim 16, wherein the base causes moisture contacting the endodontic cone to become strongly acidic.

* * * * *

UNITED STATES PATENT AND TRADEMARK OFFICE
CERTIFICATE OF CORRECTION

| | |
|---|---|
| PATENT NO. | : 7,261,562 B2 |
| APPLICATION NO. | : 10/718755 |
| DATED | : August 28, 2007 |
| INVENTOR(S) | : Wagner et al. |

It is certified that error appears in the above-identified patent and that said Letters Patent is hereby corrected as shown below:

Column 7
Line 33 Claim 3, change "CaG" to --CaO--

Column 8
Line 64 Claim 17, change "base" to --acid--

Signed and Sealed this

Fifth Day of August, 2008

JON W. DUDAS
*Director of the United States Patent and Trademark Office*